United States Patent
Thiede et al.

(12)

(10) Patent No.: US 6,255,112 B1
(45) Date of Patent: Jul. 3, 2001

(54) REGULATION OF HEMATOPOIETIC STEM CELL DIFFERENTIATION BY THE USE OF HUMAN MESENCHYMAL STEM CELLS

(75) Inventors: Mark A. Thiede, Forest Hill; Gabriel Mbalaviele, Columbia, both of MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/327,796

(22) Filed: Jun. 8, 1999

Related U.S. Application Data

(60) Provisional application No. 60/088,431, filed on Jun. 8, 1998, and provisional application No. 60/099,233, filed on Sep. 4, 1998.

(51) Int. Cl.[7] .............................. C12N 5/06; C12N 5/16
(52) U.S. Cl. ..................... 435/440; 435/347; 435/455; 435/373; 424/93.21
(58) Field of Search ..................................... 435/440, 347, 435/93.21, 455, 373

(56) References Cited

PUBLICATIONS

WO 96/09400; Kerr et al, Methods for Genetically Modifying Hematopoietic Stem Cells, Mar. 1996.*

Mbalaviele, G, Jaiswal, N, etal, Endocrinology 140:3736–3743(1999), "Human Mesenchymal Stem Cells . . . ", 1999.*

Dooley et al., J. Cel.l Physiol. 165: 386–397, 1995, Basic fibroblast growth factor and epidermal growth factor downmodulate the growth of hematopoietic cells in long–term stromal cultures, 1995.*

Koller et al., Stem Cells 15: 305–313, 1997, Importance of parenchymal:stromal cell ratio for the ex vivo reconstitution of human hematopoiesis.*

* cited by examiner

*Primary Examiner*—John S. Brusca
*Assistant Examiner*—Andrea Ousley
(74) *Attorney, Agent, or Firm*—Elliot M. Olstein; Raymond J. Lillie

(57) ABSTRACT

The invention relates to the induction of hematopoietic stem cells to differentiate into osteoclasts by culturing hematopoietic stem cells with human mesenchymal stem cells, and, in a preferred embodiment, using no exogenous cytokines. Differentiation of the mesenchymal stem cells into osteoblasts inhibited the differentiation of hematopoietic stem cells into osteoclasts. In addition, hematopoietic stem cells can be genetically engineered to carry genes of interest particularly for the expression of physiologically active proteins. In the presence of mesenchymal stem cells, the transduced cells carry the new genetic material and express gene products that can be used to modulate bone resorption.

14 Claims, 11 Drawing Sheets

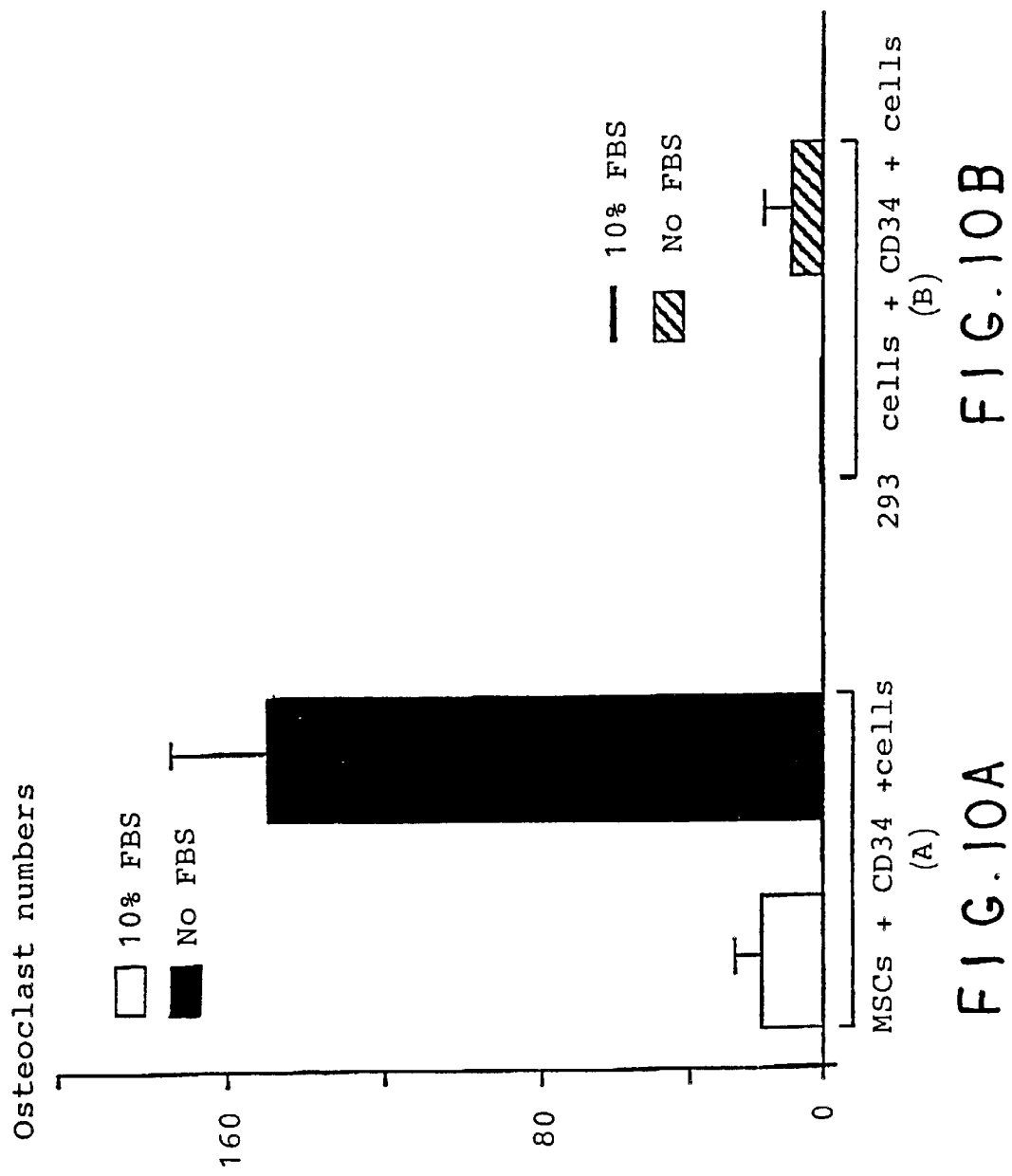

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 1
cgatcacaat ctgcagtacc                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 2
acccagtgag tcttcagtcc                                           20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 3
tttccagggc ttctttgtt                                            19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 4
cttggttgtt ggctggttc                                            19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 5
accactacta cacagacagc                                           20

<210> SEQ ID NO 6
<211> LENGTH: 20
<212> TYPE: DNA
```

-continued

```
<213> ORGANISM: Artificial Sequence
<220> FEATURE:
<223> OTHER INFORMATION: Description of Artificial Sequence:PCR primer

<400> SEQUENCE: 6
aggagaccaa agacactgca                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 7
ttctatttca gagcgcagat                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 8
agtcatgttg gagatcttgg                                                  20
```

REGULATION OF HEMATOPOIETIC STEM CELL DIFFERENTIATION BY THE USE OF HUMAN MESENCHYMAL STEM CELLS

This appln claims benefit of provisional appln No. 60/088,431 filed Jun. 8, 1998 this appln claims benefit of provisional appln No. 60/099,233 filed Sep. 4, 1998.

The present invention relates to hematopoietic stem cells and more particularly to a process and composition for differentiating human hematopoietic stem cells into a committed osteoclast lineage in the absence of exogenous osteoclastogenesis-inducing factors. The present invention further relates to genetically modified hematopoietic stem cells in the presence of human mesenchymal stem cells, such that when the hematopoietic stem cells differentiate into osteoclasts, the osteoclasts are able to express the product of the transduced gene.

BACKGROUND OF THE INVENTION

Osteoclasts are terminally differentiated hematopoietic cells responsible for physiological bone resorption. Dysfunction in osteoclast differentiation and/or activity is the cause of a variety of human metabolic bone diseases including osteoporosis (for review see Teitelbaum et al., 1995). Osteoporosis, or progressive bone loss, is attributed to a shift in the critical balance of osteoclast and osteoblast activities responsible for proper skeletal integrity. Osteoblasts, which build bone, are one terminally differentiated lineage descending from mesenchymal stem cells.

Hematopoietic progenitors in bone marrow are driven into the osteoclast cell lineage under the influence of local regulatory factors. Diverse cell types including stromal cells, which arise from mesenchymal stem cells (MSCs), are present in bone marrow. Stromal cells have been shown to produce factors that regulate osteoclast physiology (for review see Mundy et al., 1995). Histological pictures of bone show close vicinity between marrow stromal cells and hematopoietic cells. Further, the relationship between the differentiated status of bone marrow stromal cells and their potential to regulate neighboring osteoclast progenitors is poorly documented. The importance of heterotypic cell-to-cell interactions mediated by cadherin-6 between stromal cells and osteoclast progenitors using a mouse model of osteoclastogenesis has been reported (Mbalaviele et al., 1998). Several studies demonstrated that osteoclast differentiation required the presence of stromal/osteoblast cells (Takahashi et al., 1988; Mbalaviele et al., 1995). Recent studies using cells derived from rodent marrow have demonstrated that osteoprotogerin ligand (OPGL) expressed on the membrane of stromal cells is a key factor of osteoclastogenesis (Lacey et al. 1998; Kong et al. 1999). However, it has also been reported that human osteoclast cells differentiated from progenitor cells in the presence of cocktails of cytokines and that stromal cells were not necessary (Matayoshi et al., 1996). The formation of human osteoclast cells (Ocl) displaying bone-resorbing activity has been reported (Takahashi et al., 1995; James et al., 1996; Sarma et al., 1996; Quinn et al., 1997), however, critical events which take place during osteoclastogenesis are unclear.

Bone is a composite matrix consisting of both inorganic and organic elements. The organic phase contains proteins, while the inorganic component contains calcium salts. It is known that during osteoclastic bone resorption, dissolution of the inorganic phase precedes that of the organic phase and that high concentrations of calcium (>40mM) are released locally from bone matrix. In turn, increased calcium concentrations have a negative feedback on osteoclast fliction, a regulatory mechanism to prevent excessive bone resorption. Calcium is known to regulate the expression of several genes. Recently, a calcium response element that enhances human keratin-1 gene expression after exposure of keratinocytes to extracellular calcium (0.6 mM) has been characterized.

Osteoclasts are not easily isolated due to their low cell number in vivo, their fragility and tendency to adhere to other bone cells. Thus, there is a need for a method of efficiently producing quantities of osteoclasts to facilitate, for example, the design of effective therapeutics aimed at preventing abnormal osteolysis.

Accordingly, it is an object of the present invention to provide an efficient method of producing osteoclasts in vitro.

It is a further object of the invention to provide a method to produce and maintain osteoclasts in vitro without the addition of exogenous growth factors in numbers sufficient to provide an ongoing source of osteoclasts, for example, for administering osteoclasts to an individual in need thereof.

Accordingly, it is an object of the present invention to regulate hematopoietic stem cell differentiation towards osteoclast cells in the absence of exogenous growth factors, cytokines and hormones.

It is a still further object of the present invention to provide a method of producing osteoclasts from genetically modified hematopoietic cells such that when the hematopoietic cells differentiate into osteoclasts, the osteoclasts express the gene product of interest.

SUMMARY OF THE INVENTION

The present inventors have discovered that mesenchymal stem cells support osteoclast cell differentiation of hematopoietic stem cells.

Thus in one aspect of the present invention, there is provided a method for inducing the differentiation of hematopoietic progenitor cells in vitro into osteoclast cells, comprising co-culturing the hematopoietic cells with human mesenchymal stem cells.

When hematopoietic progenitor cells were co-cultured with mesenchymal stem cells, the hematopoietic progenitor cells differentiated towards osteoclast cells which were identified by the expression of markers characteristic of osteoclasts including multinuclearity, calcitonin and vitronectin receptors, and more importantly, bone resorbing activity.

It has further been discovered that the differentiation of the hematopoietic stem cells occurred in the absence of exogenous (added) growth factors, cytokines and hormones known to be required for inducing differentiation of hematopoietic stem cells.

Accordingly, one aspect of the present invention provides a method of producing osteoclasts in vitro comprising co-culturing hematopoietic stem cells with human mesenchymal stem cells. In a preferred embodiment, the cells are co-cultured in the same culture vessel such that physical cell-to-cell interactions occur between the hematopoietic progenitor cells and the mesenchymal stem cells.

It has also been discovered that when hematopoietic stem cells, which have been modified to carry exogenous genetic material of interest, are co-cultured with mesenchymal stem cells, the transduced hematopoietic stem cells differentiated into osteoclasts that also carried the new genetic material. These transduced osteoclast cells are able to express the exogenous gene product. Transduced osteoclast progenitors and the osteoclasts differentiated therefrom can be used for applications where treatment using such modified osteoclasts is beneficial, for example, in the alleviation of the effects of osteoporosis.

Accordingly, the present invention provides a method of obtaining genetically modified osteoclasts, comprising transducing hematopoietic progenitor cells with exogenous genetic material and placing the transduced hematopoietic cells under conditions suitable for differentiation of the hematopoietic stem cells into osteoclast cells which contain the exogenous genetic material.

In one embodiment, the method of producing osteoclasts comprises co-culturing transduced hematopoietic stem cells with mesenchymal stem cells such that after differentiation of the hematopoietic stem cells into osteoclasts, the osteoclasts also contain the exogenous genetic material.

The invention further relates to hematopoietic stem cells that are transduced with a polynucleotide that encodes a product that downregulates osteoclast differentiation and/or activity, and the use thereof.

In a particularly preferred embodiment, the expressed gene product downregulates osteoclast differentiation and/or activity. Hematopoietic stem cells are transduced with a retroviral vector containing a tandem of a calcium response element, tartrate resistant acid phosphatase (TRAP) promoter (specifically expressed in osteoclasts) and a nucleic acid sequence encoding an anti-osteoclast activity factor (for example, an antisense sequence to M-CSF, IL1 or IL6; an inhibitor such as an intracellular antibody to IL6, to M-CSF, to GM-CSF, to IL1, or to Leukemia Inhibitory Factor; or, an apoptotic factor). Expression of this sequence is triggered by the local increase in calcium concentration due to osteoclastic bone resorption.

It has further been found that while mesenchymal stem cells positively regulated the differentiation of $CD34^+$ progenitor cells towards osteoclast cells, MSCs that have begun differentiation into osteoblastic cells inhibited this process. In the presence of osteogenic mesenchymal stem cells, the levels of OPGL expression decreased and expression of osteoprotogerin (OPG) were found to increase. Thus, it is also contemplated that culturing hematopoietic stem cells in the presence of differentiated mesenchymal stem cells may serve to downregulate osteoclast differentiation and/or activity. Accordingly, the co-cultured cell populations of the invention may be used as part of a treatment to alleviate the symptoms of osteoporosis.

Slices were stained with toluidine blue and visualized under light microscopy. X200 magnification.

Figure 4A:
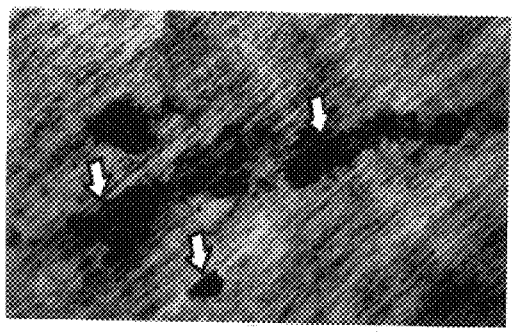
FIG. 4A shows pit formation in co-cultures of $CD34^+$ cells and MSCs (arrows).
Figure 4B:
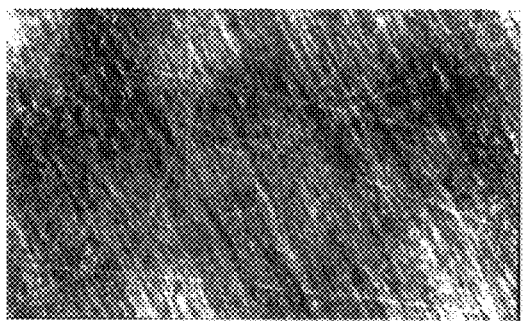
FIG. 4B shows pit formation in cultures of $CD34^+$ cells without MSCs.
Figure 4C:
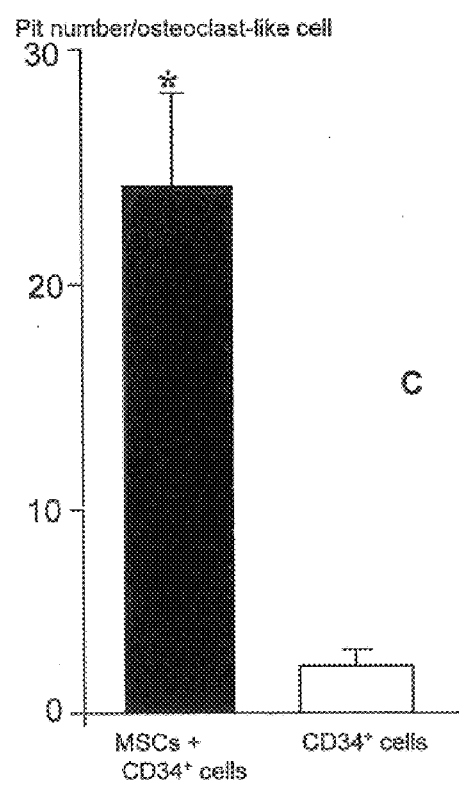

FIG. 4C shows quantitation of pits in co-cultures of $CD34^+$ cells and MSCs (closed bar) or in cultures of $CD34^+$ cells without MSCs (open bar). $*p<0.01$ versus cultures of $CD34^+$ cells without MSCs.

Figure 5B:
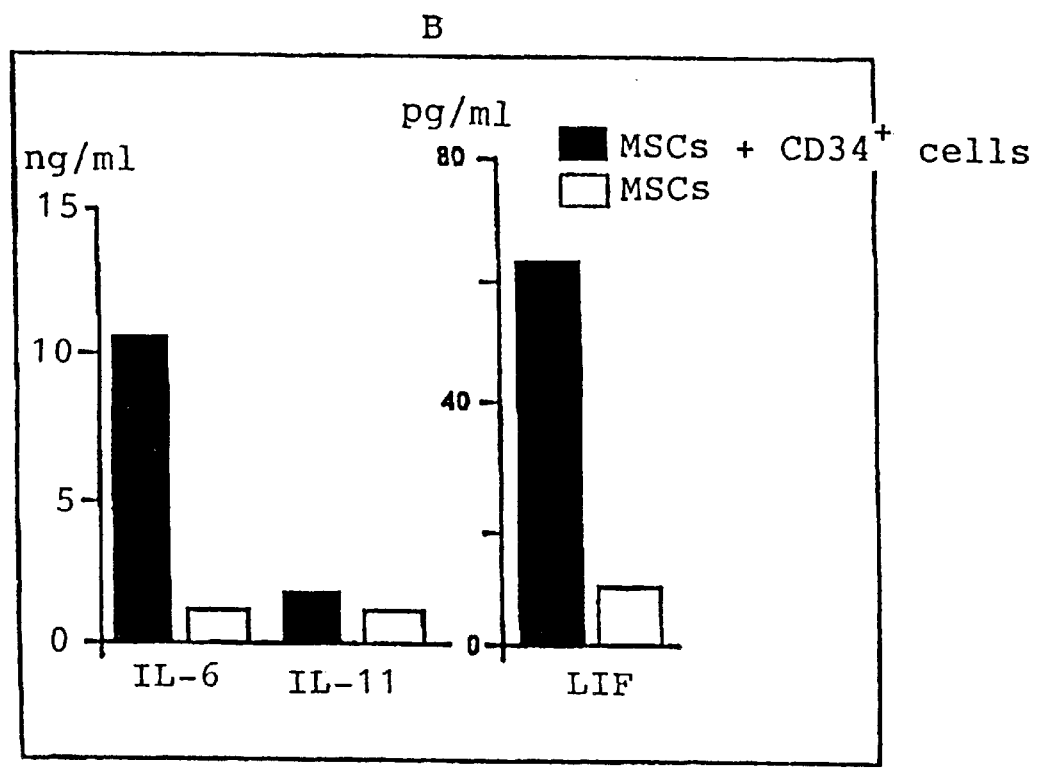
Figure 5A:
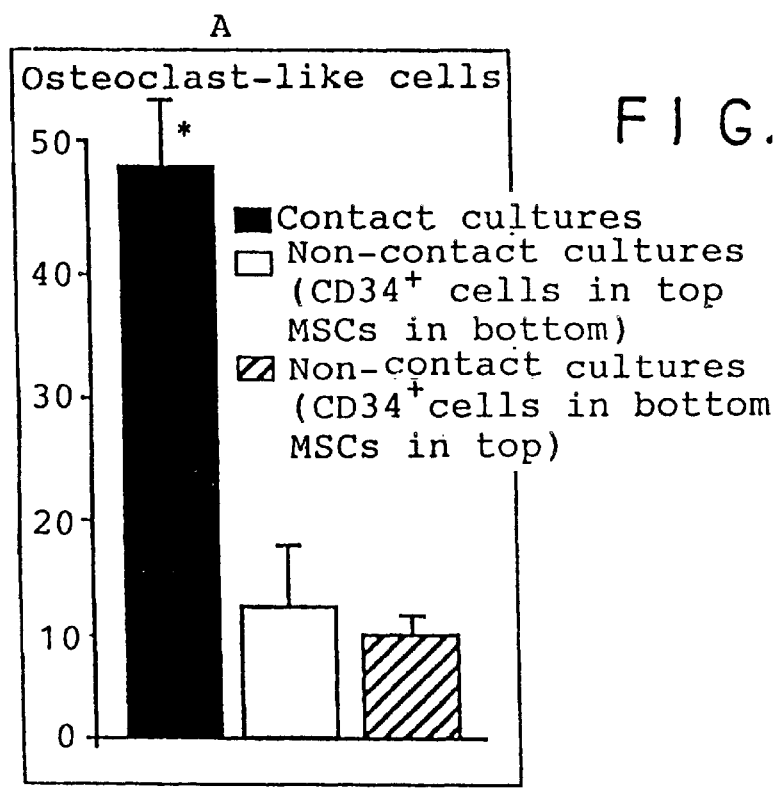

FIG. 5A shows the effects of cell-to-cell interactions in osteoclast cell formation. $CD34^+$ cells and MSCs were co-cultured in the same compartments (contact co-cultures, closed bar) or separated by means of 0.45 $\mu m$ filters (non-contact co-cultures): MSCs on top and $CD34^+$ cells on the bottom, open bar; MSCs on the bottom and $CD34^+$ cells on top, dashed bar). $*p<0.01$ versus non-contact co-cultures.

Figure 6A:
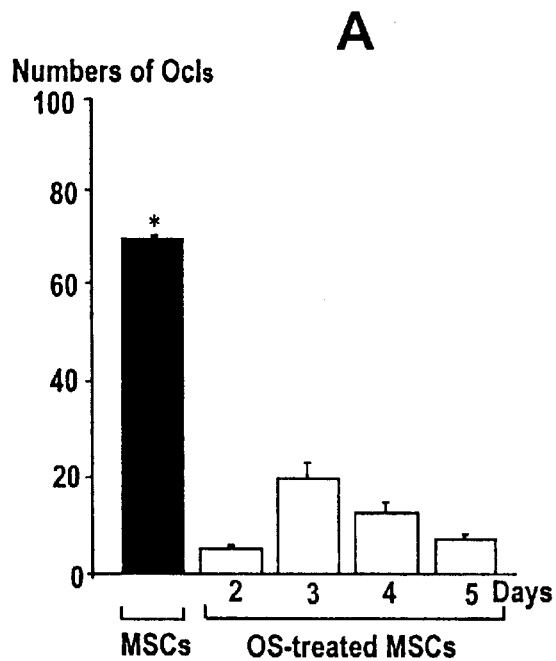
Figure 6B:
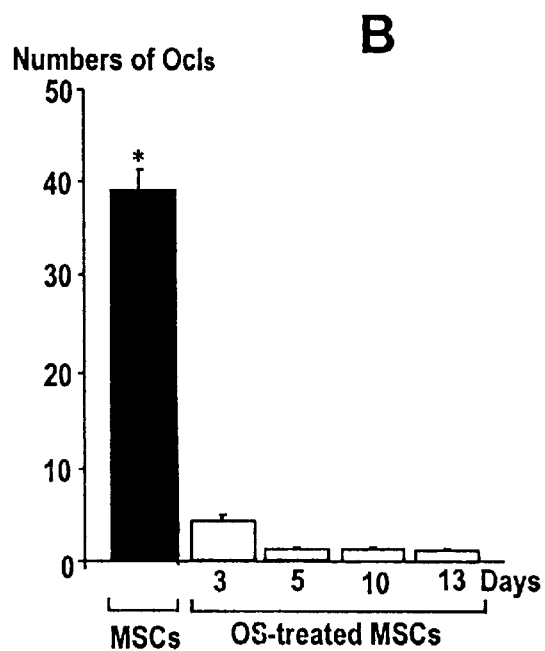

FIG. 5B shows quantitation of secreted factors (IL-6, IL-11, LIF) in co-cultures of $CD34^+$ cells with MSCs. The levels of IL-6 and LIF but not IL-11 were about 10 times higher in co-cultures of MSCs and $CD34^+$ cells compared to MSC cultures without $CD34^+$ cells FIGS. 6A and 6B show inhibition of TRAP+MNCs by osteogenic MSCs. Osteogenic differentiation of MSCs was induced by treatment with osteogenic supplement (OS) for 2, 3, 4, 5, 10 or 13 days prior to adding CD34+ cells. $*p<0.01$ versus co-cultures of OS-treated MSCs and $CD34^+$ cells.

Figure 6C:
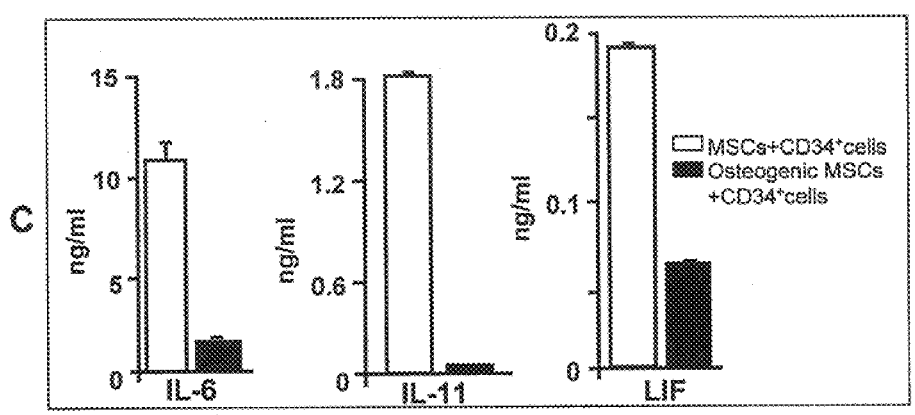

FIG. 6C shows that co-cultures of MSCs and CD34+ cells produced higher levels of IL-6, IL-11 and LIF than co-cultures of osteogenic MSCs and CD34+ cells.

Figure 6D:
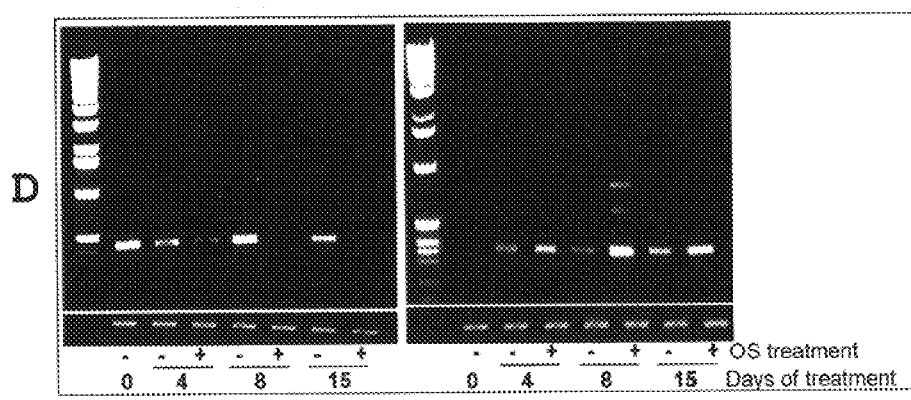

FIG. 6D shows that osteogenic differentiation of MSCs is associated with a decrease in OPGL mRNA expression (left panel) and an increase in OPG mRNA expression (right panel).

Figure 7A:
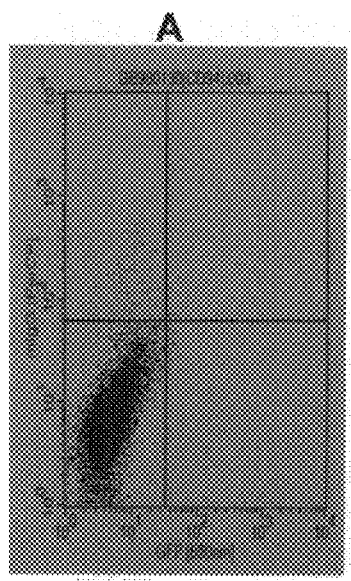

FIG. 7A shows flow cytometry analysis of $CD34^+$ cells transduced with control vector.

Figure 7B:
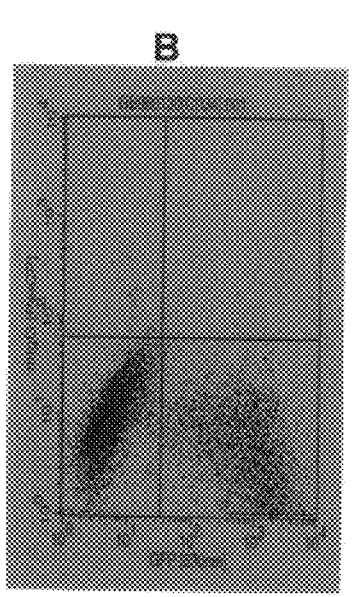

FIG. 7B shows flow cytometry analysis of $CD34^+$ cells transduced with EGFP expression vector. Approximately 30% of $CD34^+$ cells expressed EGFP.

Figure 7C:
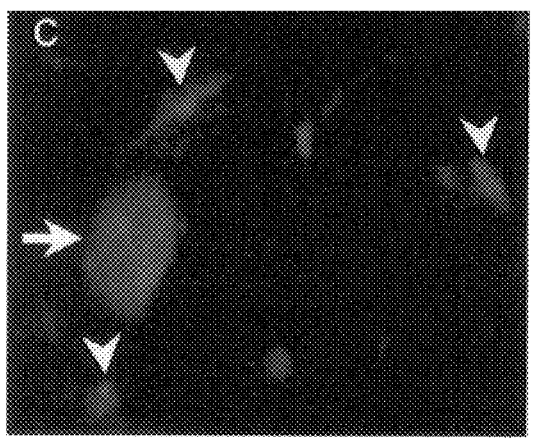

FIG. 7C shows co-cultures of MSCs with $CD34^+$ cells transduced with EGFP expression vector. EGFP was expressed by osteoclasts as well as by mononuclear cells.

Figure 7D:
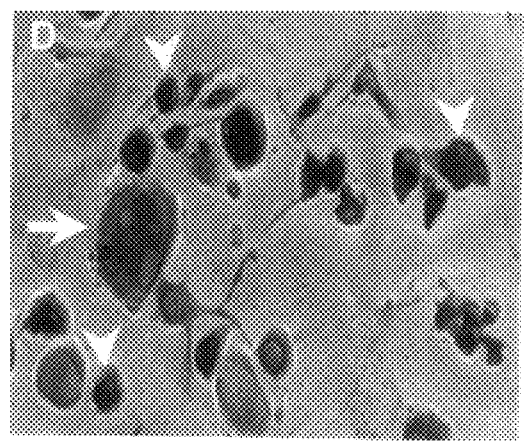

FIG. 7D shows co-cultures of MSCs with $CD34^+$ cells transduced with EGFP expression vector stained for TRAP. FIG. 7D is the light view of FIG. 7C.

Figure 8A:
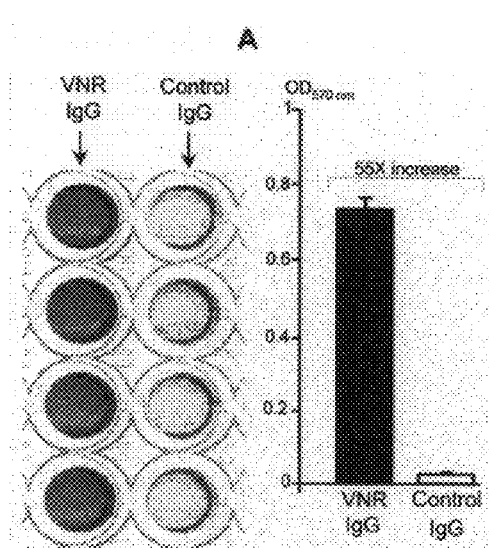

FIG. 8A shows the expression of vitronectin receptor ($\alpha_v\beta_3$) detected by ELISA. $\alpha_v\beta_3$ antibody, wells on left and closed bar; control IgG, wells on right and open bar.

Figure 8B:
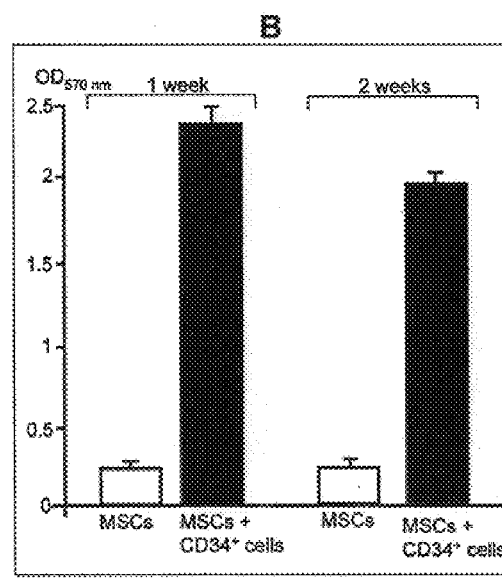

FIG. 8B shows the time-course expression of $\alpha_v\beta_3$. Co-cultures of $CD34^+$ cells and MSCs (closed bars) or MSCs without $CD34^+$ cells (open bars).

Figure 9A:
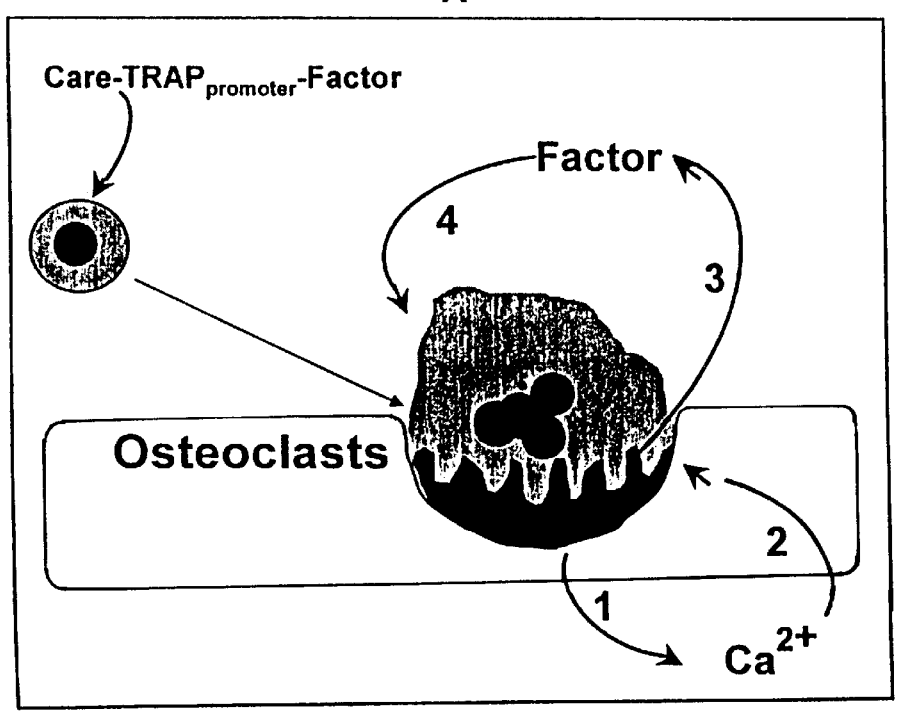

FIG. 9A shows a strategy for direct regulation of osteoclast activity.

Figure 9B:
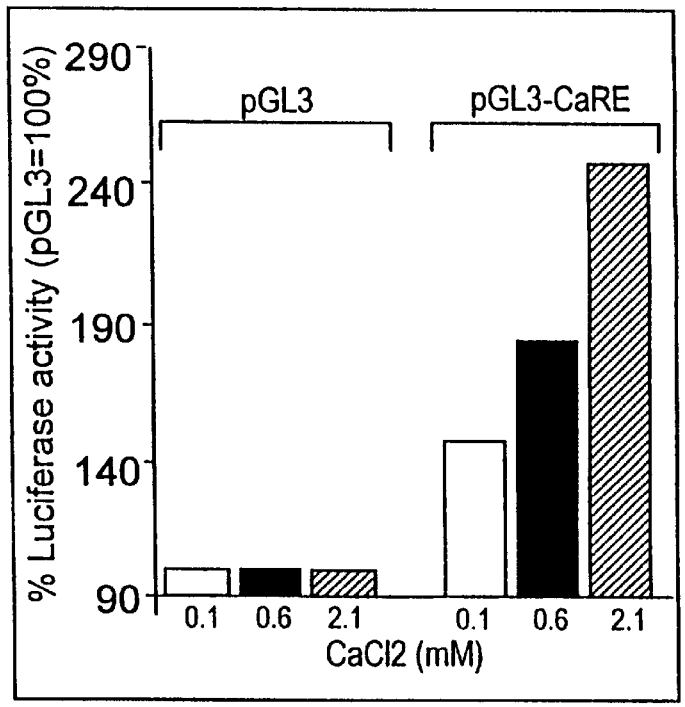

FIG. 9B shows that the addition of calcium to cultured cells transfected with a calcium-inducible expression system induced expression of the reporter gene.

FIGS. 10A–10B show the effect of serum in culture medium on production of osteoclasts in co-cultures of MSCs and CD34+ cells.

FIG. 10A shows osteoclast numbers in co-cultures of CD34+ cells and MSCs in DMEM-low glucose with 10% FBS, open bar; and in DMEM-high glucose without serum, solid bar.

FIG. 10B show co-cultures of 293 cells and CD34+ cells in DMEM-high glucose with 10% FBS, solid bar; and in DMEM-high glucose without serum, dashed bar.

DETAILED DESCRIPTION OF THE INVENTION

The present invention relates generally to the use of human mesenchymal stem cells to induce the differentiation of human CD34+ cells into osteoclast cells and compositions comprising human CD34+ cells and human mesenchymal stem cells. More particularly, the inventors found that human mesenchymal stem cells cultured in association with CD34+ cells are useful for inducing the differentiation of CD34+ cells into osteoclasts. Thus the CD34+ cells can be maintained and utilized as a source of osteoclasts.

In order to obtain subject human mesenchymal stem cells for the methods described herein, mesenchymal stem cells can be recovered from bone marrow or other mesenchymal stem cell source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood. The presence of mesenchymal stem cells in the culture colonies may be verified by specific cell surface markers which are identified with unique monoclonal antibodies, see, e.g., U.S. Pat. No. 5,486,359. These isolated mesenchymal cell population display epitopic characteristics associated only with mesenchymal stem cells, have the ability to regenerate in culture without differentiation and have the ability to differentiate into specific mesenchymal lineages when either induced in vitro or in vivo at the site of damaged tissue. Human mesenchymal stem cells are known to differentiate under the appropriate conditions into multiple cell lineages, including osteoblasts, adipocytes and chondrocytes (for review see Caplan et al., 1997).

Accordingly, any process that is useful to recover mesenchymal stem cells from human tissue may be utilized to obtain a population of cells comprising enriched mesenchymal stem cells. In one aspect, the method of isolating human mesenchymal stem cells comprises the steps of providing a tissue specimen containing mesenchymal stem cells, preferably bone marrow; isolating the mesenchymal stem cells from the specimen, for example, by density centrifugation; adding the isolated cells to a medium which contains factors that stimulate mesenchymal stem cell growth without differentiation, and allows for the selective adherence of only the mesenchymal stem cells to a substrate surface in culture; culturing the specimen-medium mixture; and removing the non-adherent matter from the substrate surface.

In a further aspect of the present invention, any process that is useful to recover hematopoietic stem cells from human tissue may be utilized to result in a population of cells comprised mostly of hematopoietic cells. Stem cells can be recovered from various types of tissue such as bone marrow and blood, including peripheral blood. The human hematopoietic stem cells can be collected from bone marrow aspirates or peripheral blood and isolated using commercially available antibodies which bind to hematopoietic stem cell surface antigens, e.g. CD34, using methods known to those of skill in the art, see e.g. U.S. Pat. No. 4,714,680. Alternatively, the hematopoietic stem cells can be recovered by depletion, i.e., by selecting out cells which express markers found on other cells. The antibodies used for these procedures may be conjugated to magnetic beads and immunogenic procedures may be utilized to recover the desired cell type.

The human mesenchymal stem cells and the hematopoietic stem cells are co-cultured under appropriate culture conditions such that the mesenchymal stem cells adhere to a substrate surface and form a monolayer. The mesenchymal stem cells are plated at a density in a range of from about $3 \times 10^3$ to about $5 \times 10^3$ cells per $cm^2$. The CD34+ cells are preferably at a cell density of approximately $5 \times 10^4$ cells per $cm^2$.

According to the method of the present invention, the isolated mesenchymal stem cells and the isolated hematopoietic progenitor cells, preferably CD34+ cells, are each culture expanded in appropriate media, i.e., cultured by methods using conditions that are apparent to those of skill in the art which favor cell growth and production of homogeneous cell populations.

The two cell populations are then co-cultured in a medium that promotes the growth of the human mesenchymal stem cells and does not adversely affect the maintenance of the hematopoietic stem cells. The media should also sustain the CD34+ cell population and support the induction of the differentiation of CD34+ cells into osteoclast cells. Suitable media are described for example in U.S. Pat. No. 5,486,359.

In a preferred embodiment, the human mesenchymal stem cells and the hematopoietic stem cells are co-cultured in Dulbecco's Modified Eagles Medium-Low Glucose (DMEM-LG #11885 Life Technologies, Gaithersburg, Md.). The medium preferably contains 10% FBS. In a particularly preferred embodiment, the human mesenchymal stem cells and the hematopoietic stem cells are co-cultured in Dulbecco's Modified Eagles Medium-High Glucose (DMEM-HG # 11995 Life Technologies, Gaithersburg, Md.) without FBS.

The hematopoietic stem cells produced according to the methods described herein can be used to provide a reliable and constant source of osteoclast cells. These osteoclasts could be used in the determination of the effects of osteotropic factors on the development and treatment of osteoporosis. It is contemplated that a ready supply of osteoclasts would be useful for screening assays for small molecule drug development, e.g., based on expression of integrin $\alpha_v\beta_3$ cell surface receptor by osteoclasts. It is believed that these cells, which have not been treated with growth factors in vitro, will have characteristics more like osteoclasts found in vivo than have heretofore been obtained.

After differentiation of the hematopoietic progenitor cells into osteoclast cells as described herein, the mixture of hematopoietic progenitor cells, osteoclasts and mesenchymal stem cells may be separated to obtain a population of cells largely consisting of the osteoclast cells. This may be accomplished by positive and/or negative selection of hematopoietic cells using antibodies to identify hematopoietic cell surface markers or other cell-type markers.

Another aspect of the present invention relates to the introduction of foreign genes into the hematopoietic progenitor cells such that progeny of the cells, the osteoclasts, carry the new genetic material.

Thus, in accordance with this aspect of the invention, the hematopoietic progenitor cells can be modified with genetic material of interest. The modified CD34+ cells can then be co-cultured in vitro with mesenchymal stem cells and induced to differentiate into osteoclast cells. The osteoclast cells are able to express the product of the gene expression or secrete the expression product. These modified cells can then be administered to a target tissue, e.g. bone marrow, where the expressed product will have a beneficial effect.

In a further embodiment, the transduced hematopoietic progenitor cells can be induced in vivo to differentiate into osteoclasts that will express the gene product. For example, the transduced hematopoietic progenitor cells in combination with mesenchymal stem cells may be administered to induce production of osteoclasts having the transduced gene. The cells may be administered in admixture with each other or separately and may be delivered to a targeted area. Alternatively, the hematopoietic progenitor cells may be used alone and caused to differentiate in vivo by mesenchymal stem cells present in vivo.

Thus, genes can be introduced into cells which are then returned to the autologous donor or an allogeneic recipient where the expression of the gene will have a therapeutic effect. For example, osteoclasts may be genetically engineered to have reduced activity in vivo. Appropriate genes would include those that play a role in the regulation of osteoporosis, in areas such as serum calcium responsiveness, estrogen secretion and bone resorption.

The hematopoietic stem cells may be genetically modified (transduced or transformed or transfected) in the presence of the human mesenchymal stem cells, wherein the mesenchymal stem cells increase the efficiency of gene transduction of the hematopoietic stem cells. Alternatively, the hematopoietic stem cells may be transduced in the absence of the human mesenchymal stem cells.

The hematopoietic stem cells may be genetically modified by incorporation of genetic material into the cells, for example using recombinant expression vectors.

As used herein "recombinant expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product The human hematopoietic progenitor cells thus may have stably integrated a recombinant transcriptional unit into chromosomal DNA or carry the recombinant transcriptional unit as a component of a resident plasmid. Cells may be engineered with a polynucleotide (DNA or RNA) encoding a polypeptide ex vivo, for example. Cells may be engineered by procedures known in the art by use of a retroviral particle containing RNA encoding a polypeptide.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is MGIN, derived from murine embryonic stem cells. Generally regarding retroviral mediated gene transfer, see McLachlin et al.(1990).

The nucleic acid sequence encoding the polypeptide is under the control of a suitable promoter. Suitable promoters which may be employed include, but are not limited to, TRAP promoter, adenoviral promoters, such as the adenoviral major late promoter; the cytomegalovirus (CMV) promoter; the respiratory syncytial virus (RSV) promoter; inducible promoters, such as the MMT promoter, the metallothionein promoter, heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the gene encoding the polypeptide. These vectors also make it possible to regulate the production of the polypeptide by the engineered progenitor cells. For example, for purposes of the present invention, the vector can contain a calcium response element. The selection of a suitable promoter will be apparent to those skilled in the art.

It is also possible to use vehicles other than retroviruses to genetically engineer or modify the hematopoietic stem cells. Genetic information of interest can be introduced by means of any virus which can express the new genetic material in such cells. For example, SV40, herpes virus, adenovirus and human papillomavirus can be used for this purpose. Other methods can also be used for introducing cloned eukaryotic DNAs into cultured mammalian cells, for example, the genetic material to be transferred to stem cells may be in the form of viral nucleic acids.

In addition, the expression vectors may contain one or more selectable marker genes to provide a phenotypic trait for selection of transformed cells such as dihydrofolate reductase or neomycin resistance.

The hematopoietic progenitor cells may be tansfected through other means known in the art. Such means include, but are not limited to transfection mediated by calcium phosphate or DEAE-dextran; transfection mediated by the polycation Polybrene; protoplast fusion; electroporation; liposomes, either through encapsulation of DNA or RNA within liposomes, followed by fusion of the liposomes with the cell membrane or, DNA coated with a synthetic cationic lipid can be introduced into cells by fusion.

The present invention further makes it possible to genetically engineer human hematopoietic progenitor cells in such a manner that they produce, in vitro or in vivo osteoclasts which produce polypeptides, hormones and proteins not normally produced in human osteoclasts in biologically significant amounts or produced in small amounts but in situations in which regulatory expression would lead to a therapeutic benefit. For example, the hematopoietic stem cells could be engineered with a gene that expresses a molecule that specifically inhibits bone resorption, but does not otherwise interfere with osteoclasts binding to bone. Alternatively the cells could be modified such that a protein normally expressed will be expressed at much lower levels. These products would then be secreted into the surrounding media or purified from the cells. The human osteoclast cells formed in this way can serve as continuous short term or long term production systems of the expressed substance.

This technology may be used to produce additional copies of essential genes to allow augmented expression by the osteoclasts of certain gene products in vivo. These genes can be, for example, hormones, matrix proteins, cell membrane proteins, cytokines, adhesion molecules, "rebuilding" proteins important in tissue repair. The expression of the exogenous genetic material in vivo, is often referred to as "gene therapy." Disease states and procedures for which such treatments have application include genetic disorders and diseases of bone and the immune system. Cell delivery of the transformed cells may be effected using various methods and includes infusion and direct depot injection into periosteal, bone marrow and subcutaneous sites.

In addition, as hereinabove described, the transduced cells may be used for in vitro production of desired protein(s). The transduced cells may further be used in screening assays for drug discovery.

In a preferred embodiment, hematopoietic stem cells are transduced with a retroviral vector containing a calcium response element, tartrate resistant acid phosphatase (TRAP) promoter and a cDNA encoding for anti-osteoclast factor.

After modification of the hematopoietic cells as described herein and induction of differentiation into osteoclasts, the mixture of hematopoietic, osteoclast and mesenchymal stem cells may be separated to obtain a population of cells largely consisting of the transduced osteoclasts. This may be accomplished by positive and/or negative selection of transduced hematopoietic cells using antibodies to identify hematopoietic cell surface markers.

The above description of the invention and the following examples are by way of illustration only. Other permutations and practices of the invention will be readily envisaged by one of ordinary skill in the art by view of the above in conjunction with the appended drawings. Therefore, such permutations and variations are within the scope of the present invention.

EXAMPLES

Statistical Analysis All data were analyzed by a paired t test. Samples were run in triplicates and data shown were means+ SE.

Example 1

Cell isolation Bone marrow samples were collected from healthy human donors at the Johns Hopkins University under an Institutional Review Board-approved protocol. Mesenchymal stem cells (MSCs) were isolated and cultured according to known methods (Majumdar et al., 1998). When the cultures reached 90% confluence, adherent cells were recovered by the addition of a solution containing 0.25% trypsin-EDTA (Life Technologies) and replated at a density of $1 \times 10^6$ cells per 185 cm$^2$ flask as passage-1 cells.

CD34+ cells, isolated from bone marrow of healthy patients were obtained from Poietic Technologies, Gaithersburg, Md.). They were immunopurified to 95% purity using antibody to CD34 conjugated to magnetic beads (CD34+ cell separation column: Miltenyi Biotec, Auburn, CA Ab:QBEND.10) and cryopreserved.

Co-cultures MSCs of early passage (2 to 3) were plated at $3 \times 10^3$ cells per cm$^2$ and cultured until sub-confluency in DMEM LG+10% FBS. CD34$^+$ cells were then added at $5 \times 10^4$ cells per cm$^2$ to MSC cultures. Cultures were maintained for 3 weeks at 37° C. in an atmosphere of 95% air/5% $CO_2$ and fed every three days with the medium. Because most of the CD34+ cells remained non-adherent, half of the culture medium was gently aspirated without agitating non-adherent cells and replaced with fresh medium.

TRAP staining After three weeks, cells were fixed in 60% acetone in citrate buffer (pH 5.4) for 30 seconds, washed twice with distilled water, air-dried, and stained for tartrate-resistant acid phosphatase (TRAP), a widely-used cytochemical marker of mouse osteoclasts (Wijngaert and Burger, 1986), using a commercially available kit (Sigma, St Louis, Mo.). Stained cultures were examined under light microscopy at a magnification of X200. TRAP-positive (red-staining) multinucleated (three or more nuclei) osteoclasts in each well were counted by manually scanning across the entire well in a systematic fashion (Mbalaviele et al., 1998).

Figure 1A:
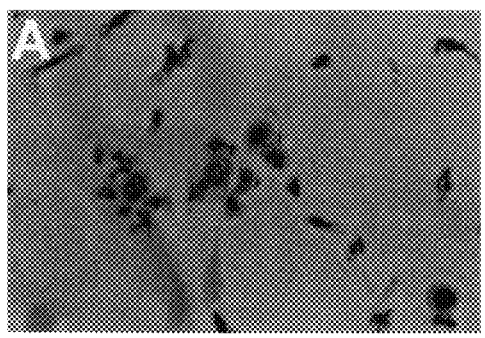
FIG. 1A shows TRAP staining of $CD34^+$ cells cultured in the absence of mesenchymal stem cells (MSCs).
Figure 1B:
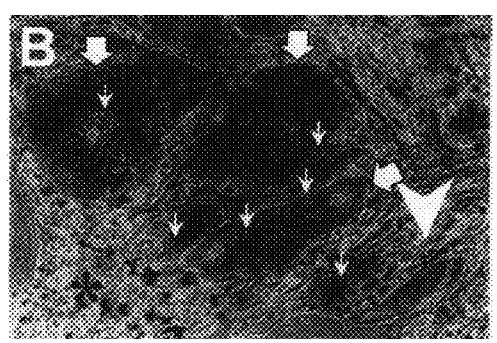
FIG. 1B shows TRAP staining of $CD34^+$ cells cultured in the presence of MSCs. Many multinucleated $TRAP^+$ cells (TRAP+MNCs) (arrow) as well as mononuclear $TRAP^+$ cells were formed in the presence of MSCs which appeared as a confluent layer of spindle-shaped cells (arrowhead). Small arrows and star indicate clusters of nuclei.
Figure 1C:
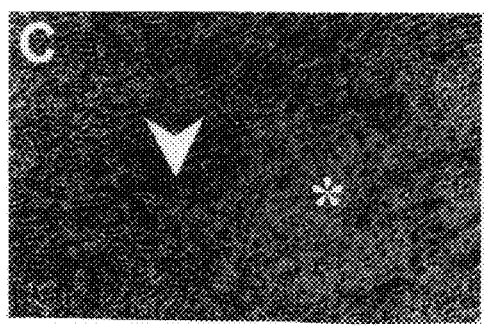
FIG. 1C shows staining of $CD34^+$ cells cultured in the presence of human skin fibroblasts (SK1087 cells; arrowhead). No TRAP+MNCs were formed.
Figure 1D:
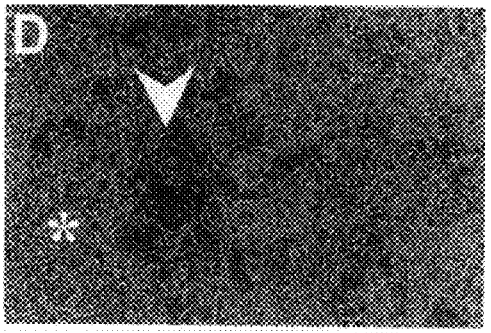
FIG. 1D shows staining of $CD34^+$ cells cultured in the presence of human kidney cells (293T; arrowhead). TRAP+MNCs were not formed.

CD34$^+$ cells cultured in the absence of MSCs or cytokines/growth factors failed to form multinucleated cells expressing tartrate-resistant acid phosphatase (TRAP+ MNCs) (FIG. 1A). MSCs supported the differentiation of co-cultured CD34$^+$ cells towards osteoclast cells (FIG. 1B). In contrast, human slin fibroblasts (SK1087 cells) or human kidney cells (293T) failed to support the formation of TRAP+MNCs (FIGS. 1C and 1D, respectively). Treatment of CD34$^+$ cells with IL-1, IL-3 and GM-CSF in the absence of MSCs yielded the formation of osteoclast cells, but the numbers of these cells were lower compared to those present in CD34$^+$/MSCs co-cultures (data not shown).

Example 2

Figure 2A:
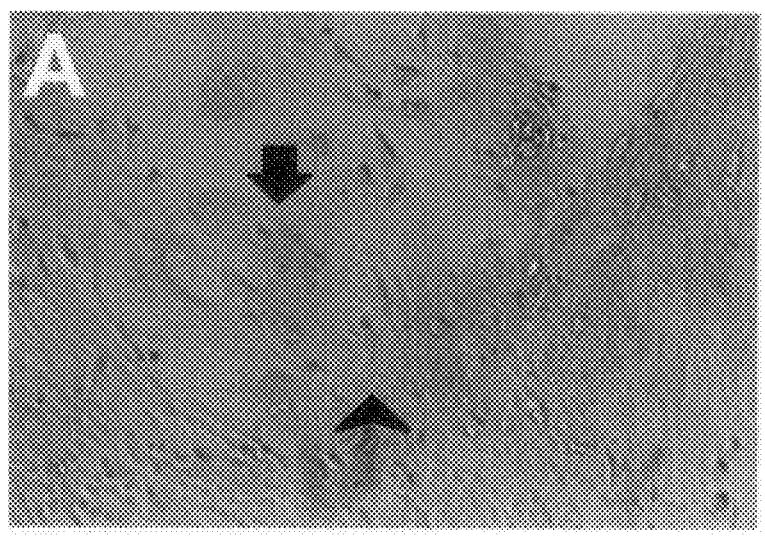
FIG. 2A shows immunocytochemical staining of co-cultures of $CD34^+$ and MSCs with negative-control antibody.
Figure 2B:
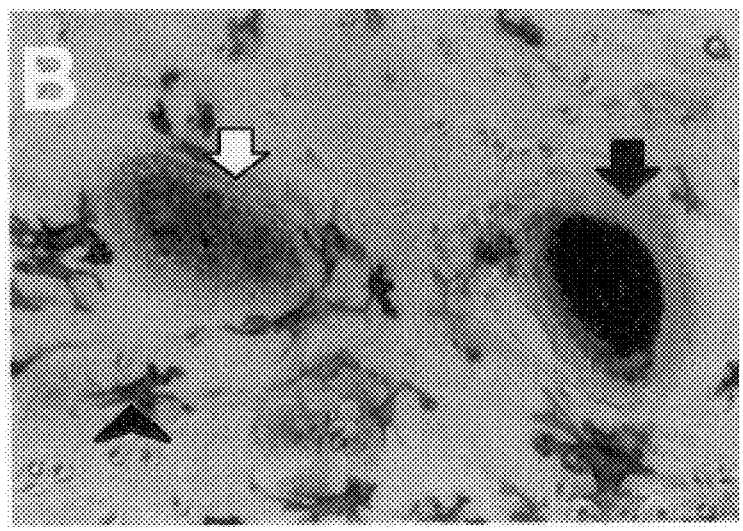
FIG. 2B shows immunocytochemical staining of co-cultures of $CD34^+$ and MSCs with antibody recognizing vitronectin receptor.

Immunocytochemistry CD34$^+$ cells and MSCs co-cultured for three weeks were fixed with a fresh solution of 3.7% (wt./vol.) formaldehyde in PBS, blocked with 1.5% horse serum, incubated with the monoclonal antibody to human integrin $\alpha v \beta 3$ (Dr. Horton, The Rayne Institute, London, England) at 1:50 dilution in PBS containing 0.15% horse serum. Cells were then incubated with glucose oxidase-conjugated goat secondary antibody using Vectastain ABC-GO kit (Vector Laboratories, Inc., Burlingame, Calif.). All incubations were performed at room temperature for 30 minutes followed by washing 3 times with PBS. Results are shown in FIG. 2. Osteoclast cells (black arrow) and their precursors (arrowhead) were stained by vitronectin receptors antibody but not by the control antibody. MSCs did not show any staining with the receptor antibody. Multinucleated cells expressing low levels of vitronectin receptors were seen in co-cultures (FIG. 2B, white arrow).

RNA Preparation and RT-PCR Total RNA was extracted from MSC cultures or co-cultures of CD34$^+$ and MSCs using High Pure RNA Isolation kit purchased from Boehringer Mannheim (Indianapolis, Ind.). PCR was performed for 30 cycles either on reverse-transcribed single-strand cDNA from total RNA preparations (1 $\mu$g) using GeneAmp RT-PCR method under the conditions described by the supplier (Perkin Elmer, Foster City, Calif.) with the following modifications: denaturation at 95° C. for 20 seconds, annealing at 55° C. for 20 seconds, polymerization at 72° C. for 30 seconds and elongation at 72° C. for 10 minutes. The upstream and downstream primers, respectively, were designed as follows: TRAP: 5'-CGATCACAATCTGCAGTACC-3'(SEQ ID NO: 1) and 5'-ACCCAGTGAGTCTTCAGTCC-3' (SEQ ID NO:2), PCR product size=150 bp; calcitonin receptor (CTR): 5'-TTTCCAGGGCTTCTTGTT-3' (SEQ ID NO:3) and 5'-CTTGGTTGTTGGCTGGTTC-3' (SEQ ID NO:4), PCR product size-205 bp. PCR products were size-fractionated by 1% agarose gel electrophoresis.

Figure 3:
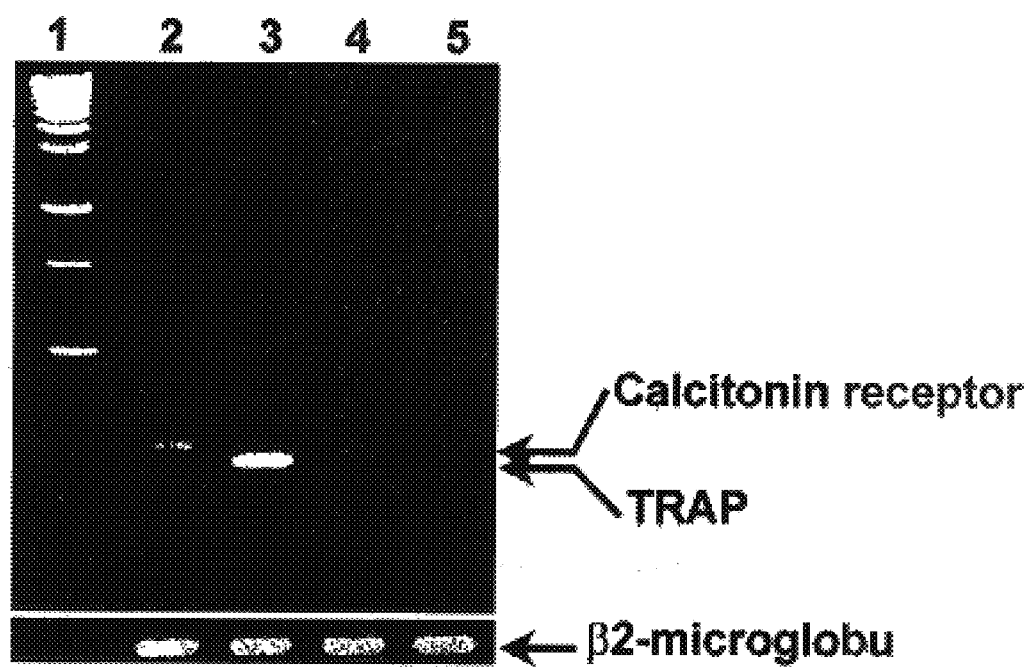
FIG. 3 shows RT-PCR of RNA purified from co-cultures of MSCs and $CD34^+$ cells (lanes 2–3) or cultures of MSCs without $CD34^+$ cells (lanes 4–5). Calcitonin receptors (lanes 2 and 4) and TRAP (lanes 3 and 5) were only detected in samples from co-cultures of MSCs and $CD34^+$ cells. The conserved and unspliced region of the calcitonin receptor family was chosen to design primers. Lane 1, 1 kb DNA ladder; bottom, $\beta2$-microglobulin.

RT-PCR analysis showed expression of TRAP and calcitonin receptors by cells derived from CD34+ cells, the osteoclast lineage (Lanes 2 and 3 of FIG. 3). These proteins were not expressed by MSCs.

Example 3

Pit formation assay To further confirm the presence of osteoclast cells in the cultures, the ability of cells produced in co-cultures of CD34+ cells and MSCs to form pits was examined, an indication of osteoclastic bone resorption. Elephant smoothened tusk slices were sterilized with 200-proof ethanol, air-dried and washed several times with PBS. MSCs were plated at $3 \times 10^3$ cells per $cm^2$ on the tusk slices (4×4×0.1 mm) in 96-well plates and cultured for a week in hMSC medium pH 7.4. CD34+ cells were then added at $5 \times 10^4$ cells per $cm^2$. Artificial bone analog, osteologic discs (Millenium Biologix Inc., Ontario, Canada) were used to establish the optimal conditions of the assay. At the end of the 3-week culture period, the cells on slices were stained for TRAP, counted, then removed with 0.1 M NaOH in water followed by ultrasonication for 2 minutes. The bone slices were stained for 5 minutes with 1% toluidine blue prepared in distilled water containing 1% sodium borate. The numbers of pits were counted under light microscope as previously described (Prallet et al., 1992). Authentic resorption pits were found on bone analog as well as on elephant tusk slices when CD34+ cells were co-cultured with MSCs (FIG. 4).

Example 4

Effects of cell-cell interactions CD34+ cells and MSCs were either cultured in the same compartment (contact co-cultures) or in two different compartments (non-contact co-cultures) separated by culture proof inserts with a 0.45 $\mu$m porous membrane (Becton Dickinson, Bedford, Mass.) to investigate physical cell-cell interactions. The results shown in FIG. 5A indicated that osteoclast cells were formed in the contact cultures, and there were about two-thirds less osteoclast cells in non-contact cultures, regardless of in which compartment (top or bottom) the MSCs or CD34+ cells were seeded.

Example 5

Interactions through secreted factors CD34+ cells were co-cultured with MSCs. Conditioned media were collected after two days from MSCs cultured in the absence or presence of CD34+ cells. The protein levels of cytokines IL-1α, IL-6, IL-11, granulocyte/macrophage-colony stimulating factor (GM-CSF) and leukaemia inhibitory factor (LIF) secreted into the hematopoietic stem cell and mesenchymal stem cell co-cultures were measured using a Quantikine kit (R&D Systems, Minneapolis, Minn.).

FIG. 5B shows the levels of IL-6, IL-11 or LIF in co-cultures of CD34+ cells and MSCs. The levels of IL-1α and GM-CSF were undetectable. The levels of IL-6 and LIF were about 10 times greater in co-cultures of MSCs and CD34+ cells compared to MSCs cultures without CD34+ cells. The levels of IL-1α and GM-CSF were undetectable.

Example 6

Effects of osteogenic MSCs (differentiated MSCs) Osteogenic differentiation of MSCs was induced by treating MSCs with osteogenic supplement (OS) containing 100 mM dexamethasone 10 mM β-glycerophosphate and 50 $\mu$M L-ascorbic acid-2 phosphate for 2, 3, 4, 5, 10 or 13 days. At the time of the co-culture with CD34+ cells, OS containing medium was replaced with medium without OS. FIGS. 6A and 6B show that osteogenic MSCs inhibited TRAP+MNC formation compared to MSCs. FIG. 6C shows the levels of IL-6, IL-11 or LIF in co-culture. The levels of IL-6, IL-11 and LIF were higher in co-cultures of MSCs with CD34+ cells compared to cocultures of osteogenic MSCs and CD34+ cells.

RNA preparation andRT-PCR Total RNA isolation and RT-PCR analysis were carried out as described in example 2. The upstream and downstream primers, respectively, for OPG were 5'-ACCACTACTACACAGACAGC-3' (SEQ ID NO:5) and 5'-AGGAGACCAAAGACA CTGCA-3' (SEQ ID NO:6); for OPGL 5'-TTCTATTTCAGAGCGCAGAT-3' (SEQ ID NO:7) and 5'-AGTCATGTTGGAGATCTTGG-3' (SEQ ID NO:8).

FIG. 6D shows that treatment of MSCs with OS for 4, 8, or 15 days decreased the expression of OPGL RNA. In contrast, treatment of MSCs with OS for 4, 8 or 15 days increased the expression of OPG mRNA.

Example 7

Transduction of CD34+ cells The construction of the retroviral vector MGIN expressing enhanced green fluorescent protein (EGFP) gene and the production of the retroviral supernatants has been previously reported (Cheng et al., 1997). Briefly, MGIN is a murine embryonic stem cell virus-based vector containing EGFP gene and the internal ribosome entry site (IRES). Amphotropic supernatants produced by PA317 packaging cells were made from selected producers after infection by BOSC23 ecotropic viral stocks. For transduction, previously frozen vector supernatants were mixed at a 1:1 ratio with medium containing CD34+ cells in the presence of 8 $\mu$g/ml polybrene (Sigma, St. Louis, Mo.), interleukin-3 (IL-3) and IL-6 (10 ng/ml, each), stem cell factor (SCF) and Flk2 (FL) (100 ng/ml, each). Control cells were transduced with non-EGFP-expressing vector. The transduction mixture was then centrifuged at 1800 g at 32–35° C. After a 4-hour "spinoculation," cells were washed once and cultured for 24 hours in medium containing the above growth factors. After the transduction was repeated once more, a cell fraction was analyzed by flow cytometry to test transduction efficiency while the remaining cells were used for the osteoclastogenesis assay. The transduced CD34+ cells were co-cultured for three weeks without added factors. The co-cultures were stained for TRAP as described in example 1. Cells were visualized with a fluorescence microscope to detect EGFP or under a light microscope to detect TRAP.

Flow cytometry analysis results are shown in FIG. 7. FACS analysis showed that 30% of CD34+ cells transduced with EGFP vector expressed the transgene (FIG. 7B). Co-cultures of transduced CD34+ cells with MSCs yielded osteoclasts expressing both EGFP (FIG. 7C) and TRAP (FIG. 7D).

Example 8

Detection of vitronectin receptor by ELISA MSCs were plated at $3 \times 10^3$ cells per $cm^2$ and cultured in hMSC medium until subconfluency. CD34+ cells were then added at $2.5 \times 10^4$ cells per $cm^2$ to MSC cultures. Cultures were maintained for 1, 2 or 3 weeks. Cells were fixed with 3.6% formaldehyde and blocked with 10% goat serum for 30 minutes, followed by incubation with the antibody to the vitronectin receptor (αvβ3). With extensive washes between additions, a biotin-labeled secondary antibody was added (goat antimouse IgG; Pierce, Rockford, Ill.) followed by streptavidin-conjugated β-galactosidase (Gibco BRL) for 1 hour. The soluble substrate chlorophenol red-β-D-galactopyranoside (CPRG; Boehringer Mannheim, Indianapolis, Ind.) was then added, and color development was read at 570 nm after 30 minutes. Control primary antibodies were also run for each treatment and this background measurement was subtracted from the readings for each well. ELISA results are presented in FIG. 8 as mean absorbance units, with background subtracted. The vitronectin receptor (αvβ3) was detected by the specific antibody but not by the control antibody (FIG. 8A). αvβ3 expression by the osteoclast cell lineage was induced after 1 week of co-cultures and was less expressed by MSCs (FIG. 8B).

Example 9

Hematopoietic stem cells as therapeutic targets Hematopoietic stem cells (HSCs) are transduced with a retroviral vector containing a calcium response element, tartrate resistant acid phosphatase (TRAP) promoter and a cDNA encoding for anti-osteoclast factor (antisense, inhibitor, apoptotic factor) (see FIG. 8). TRAP promoter has been used to specifically target the osteoclast cell lineage. Transduced-HSCs are infused to osteoporotic patients. They home to bone marrow, engraft and differentiate into osteoclasts. The osteoclasts respond to local high calcium concentrations generated by excessive bone resorption (steps 1 and 2), by expressing an anti-osteoclast factor (step 3) which stops osteoclast activity (step 4). One such factor is Osteoprotegerin (OPG) which when secreted has been demonstrated to decrease bone resorption (osteopetrosis) and appears to generally block osteoclastogenesis (Simonet (1997)). The transduced hematopoietic cells can also be induced to differentiate into osteoclasts ex vivo, and then infused to osteoporotic patients.

Calcium-response element (CaRE) was cloned under the control of CMV promoter within pGL3 vector that contains luciferase as a reporter gene (Promega Madison, Wis.) to yield pGL3-CaRE. pGL3 or pGL3-CaRE were transfected into human kidney cell line 293T using a calcium phosphate co-precipitation method. Cells were then cultured in the presence of increasing concentrations of calcium. Luciferase activity was assessed using Dual-Luciferase™ reporter assay system (Promega). The data show that calcium as low as 0.1 mM induced luciferase activity in pGL3-CaRE but not in pGL3 (FIG. 9B).

Example 10

Effect of serum in culture medium Co-cultures of MSCs and CD34+ cells were studied to determine the effect of serum on the production of osteoclasts. Co-cultures of CD34+ cells and MSCs were cultured, under the conditions described above, however the media tested were DMEM-low glucose with 10% FBS and DMEM-high glucose without serum. Control cultures contained human kidney cell line 293 cells co-cultured with CD34+ cells in DMEM-high glucose with and without serum. The cultures were terminated at 12 days rather than 21 days as in the experiments in the foregoing examples.

The results shown in FIG. 10 demonstrate that co-culturing MSCs and CD34+ cells in DMEM-high glucose without FBS yielded a greater number of osteoclasts than co-culture in the standard DMEM-LG with 10% FBS.

CITED LITERATURE

Caplan AI, Bruder SP: Cell and molecular engineering of bone regeneration, in Lanza R, Langer R, Chick W (eds): Textbook of Tissue Engineering, Georgetown, Landes Company, 1997, p 603

Cheng L, Du C, Murray D, Tong X, Zhang YA, Chen BP, Hawley RG: A GFP reporter system to assess gene transfer and expression in human hematopoietic progenitor cells. *Gene Therapy* 4:1013 (1997)

James IE, Dodds RA, Lee-Rykaczewski E, Eichman CF, Connor JR, Hart T, Maleef BE, Lackman RD, Gowen M: Purification and characterization of fully functional human osteoclast precursors. *J. Bone Min. Res.* 11: 1608 (1996)

Kong YY, Yoshida H, Sarosi I, Tan HL, Timms E, Capparelli C, Morony S, Oliveira-dos-Santos AJ, Van G, Itie A, Khoo W, Wakeham A, Dunstan CR, Lacey DL, Mak TW, Boyle WJ, Penninger JM: OPGL is a key regulator of osteoclastogenesis, lymphocyte development and lymph-node organogenesis. *Nature* 397(6717):315–23 (1999)

Lacey DL, Timms E, Tan HL, Kelley MJ, Dunstan CR, Burgess T, Elliott R, Colombero A, Elliott G, Scully S, Hsu H, Sullivan J, Hawkins N, Davy E, Capparelli C, Eli A, Qian YX, Kaufman S, Sarosi I, Shalhoub V, Senaldi G, Guo J, Delaney J, Boyle WJ: Osteoprotegerin ligand is a cytokine that regulates osteoclast differentiation and activation. *Cell* 93(2):165–76 (1998)

McLachlin et al. Progress in Nucleic Acid Research and Molecular Biology, 38:91–135(1990)

Majumdar MK, Thiede MA, Mosca JD, Moorman M, Gerson S: Phenotypic and functional comparison of cultures of marrow-derived mesenchymal stem cells (MSCs) and stromal cells. *J Cell. Physiol.* 176(1):57–66 (1998)

Matayoshi A, Brown C, DiPersio JF, Haug J, Abu-Amer Y, Liapis H, Kuestner R, Pacifici R: Human blood-mobilized hematopoietic precursors differentiate into osteoclasts in the absence of stromal cells. *Proc. Natl. Acad. Sci. USA* 93, 10785 (1996)

Mbalaviele G, Orcel P, Morieux C, Nijweide PJ, Devemejoul MC: Osteoclast formation from human cord blood mononuclear cells co-cultured with mice embryonic metatarsals in the presence of M-CSF. *Bone* 16: 171 (1995)

Mbalaviele G, Nishimura R, Myoi A, Niewolna M, Reddy SV, Chen D, Feng J, Roodman D, Mundy GR, Yoneda T: Cadherin-6 mediates the heterotypic interactions between the hemopoietic osteoclast cell lineage and stromal cells in a murine model of osteoclast differentiation. *J. Cell Biol* 141(6):1467–1476 (1998).

Mundy GR, Boyce BF, Yoneda T, Bonewald LF, Roodman GD: Cytolines and bone remodeling, in Marcus R, Feldman D, Kelsey J (eds): *Osteoporosis*, San Diego, Academic Press, 1995, p302

Prallet B, Male P, Neff L, Baron R: Identification of a functional mononuclear precursor of the osteoclast in chicken medullary bone marrow cultures. *J Bone Min. Res.* 7: 405 (1992)

Sarma U, Flanagan AM: Macrophage colony-stimulating factor induces substantial osteoclast generation and bone resorption in human bone marrow cultures. *Blood*, 88: 2531 (1996)

Quinn JMW, Fujikawa Y, McGee JO'D, Athanasou NA: Rodent osteoblast-like cells support osteoclastic differentiation of human cord blood monocytes in the presence of M-CSF and 1,25 Dihydroxyvitamin D3. *Int. J. Biochem. Cell Biol.* 29: 173 (1997)

Simonet et al. Osteoprotegerin: A Novel Secreted Protein Involved in the Regulation of Bone Density. *J. Biol. Chem.* 268(1):377–384 (1993)

Takahashi S, Reddy SV, Dallas M, Devlin R, Chou JY, Roodman GD: Development and characterization of a human marrow stromal cell line that enhances osteoclast-like cell formation. *Endocrinol.* 136: 1441 (1995)

Takahashi S. et al. *Endocrinology* 123:2600–2602 (1988)

Teitelbaum SL, Tondravi MM, Ross FP: Osteoclast biology, in Marcus R, Feldman D, Kelsey J (eds): *Osteoporosis*, San Diego, Academic Press, 1995, p 61

Wijngaert FB, Burger EH: Demonstration of tartrate-resistant acid phosphatase in undecalcified, glycomethacrylate-embedded mouse bone: a possible marker for (pre-osteoclast identification *J Histol.Cytol.* 34:1317 (1986)

We claim:

1. A method for producing osteoclasts in vitro comprising co-culturing mesenchymal stem cells with hematopoietic stem cells such that the hematopoietic stem cells produce osteoclasts.

2. The method of claim 2 wherein co-culturing is done in the absence of exogenous cytokines.

3. The method of claim 1 wherein the hematopoietic stem cells are CD34+ cells.

4. The method of claim 1 wherein the hematopoietic stem cells and the mesenchymal stem cells are in contact.

5. A method of producing genetically modified osteoclasts, comprising transducing hematopoietic progenitor cells with exogenous genetic material; and culturing the transduced hematopoietic cells in the presence of mesenchymal stem cells to induce differentiation of the transduced hematopoietic cells into osteoclasts that contain the exogenous genetic material.

6. The method of claim 5 wherein the transduced hematopoietic stem cells are induced to differentiate in vitro.

7. The method of claim 5 wherein the transduced hematopoietic stem cells are induced to differentiate in vivo.

8. A method of obtaining genetically modified osteoclasts comprising transducing hematopoietic progenitor cells with exogenous genetic material and placing the transduced hematopoietic cells under conditions suitable for differentiation of the hematopoietic stem cells into osteoclast cells that contain the exogenous genetic material.

9. The method of claim 8 wherein the hematopoetic cells are differentiated in vivo.

10. The method of claim 8 wherein the hematopoietic cells are administered in vivo with human mesenchymal stem cells.

11. A composition comprising genetically modified osteoclasts.

12. The composition of claim 11 wherein the genetically modified osteoclasts are human.

13. The composition of claim 12 wherein the genetically modified osteoclasts are not immortal.

14. A method for inibiting differentiation of hematopoietic stem cells into osteoclasts comprising co-culturing differentiating mesenchymal stem cells with hematopoietic stem cells such that osteoclastogenesis is inhibited.

* * * * *